(12) United States Patent
Arav

(10) Patent No.: US 7,331,186 B2
(45) Date of Patent: Feb. 19, 2008

(54) CHANGING THE TEMPERATURE OF A LIQUID SAMPLE AND A RECEPTACLE USEFUL THEREFOR

(75) Inventor: Amir Arav, Tel-Aviv (IL)

(73) Assignee: I.M.T. Interface Multigrad Technology Ltd, Ness Ziona (IL)

( * ) Notice: Subject to any disclaimer, the term of this patent is extended or adjusted under 35 U.S.C. 154(b) by 119 days.

(21) Appl. No.: 10/519,222

(22) PCT Filed: Feb. 10, 2003

(86) PCT No.: PCT/IL03/00101

§ 371 (c)(1),
(2), (4) Date: Apr. 11, 2005

(87) PCT Pub. No.: WO2004/003444

PCT Pub. Date: Jan. 8, 2004

(65) Prior Publication Data

US 2005/0223716 A1    Oct. 13, 2005

(51) Int. Cl.
F25D 25/00 (2006.01)
F25D 17/02 (2006.01)

(52) U.S. Cl. .............................. 62/62; 62/64
(58) Field of Classification Search .................. 62/62, 62/64, 65, 78, 373
See application file for complete search history.

(56) References Cited

U.S. PATENT DOCUMENTS 2,654,250 A * 10/1953 Harrington ............... 73/864.61
3,347,101 A * 10/1967 Kennedy ................. 73/863.11
3,794,566 A * 2/1974 Raal ........................ 202/160
4,212,171 A * 7/1980 Soecknick ..................... 62/63
4,972,681 A * 11/1990 Lofkvist ..................... 62/374
5,715,686 A * 2/1998 Arav ......................... 62/54.1
5,873,254 A    2/1999 Arav
6,166,761 A * 12/2000 Arav ......................... 348/80
6,176,089 B1 * 1/2001 Bouche ....................... 62/64
6,223,541 B1 * 5/2001 Farrag ........................ 62/62
6,615,592 B2 * 9/2003 Prien et al. ................. 62/64
6,635,414 B2 * 10/2003 Wisniewski ............... 435/1.3
6,691,608 B1 * 2/2004 Thompson ................. 99/483
6,858,424 B2 * 2/2005 Wisniewski ............ 435/307.1
6,916,602 B2 * 7/2005 Arav ........................ 435/1.3
6,955,793 B1 * 10/2005 Arencibia, Jr. ............ 422/202
7,087,876 B2 * 8/2006 Petrenko .................... 219/770

FOREIGN PATENT DOCUMENTS

| FR | 2 574 919 | | 6/1986 |
| JP | 2-307324 A | * | 12/1990 |
| RU | 2178554 C2 | * | 1/2002 |
| WO | 03/020874 A3 | | 3/2003 |
| WO | 03/056919 A3 | | 7/2003 |

* cited by examiner

Primary Examiner—Mohammad M. Ali
(74) Attorney, Agent, or Firm—The Nath Law Group; Susanne M. Hopkins; Ari G. Zytcer

(57) ABSTRACT

Disclosed is a method of changing the temperature of a liquid sample, comprising: providing a receptacle having inner and outer walls defining an annular portion therebetween for receiving therein a liquid sample, inserting said liquid sample, at a first temperature, into said annular portion, and exposing said receptacle to a second temperature different from said first temperature. Further disclosed are a receptacle useful in the above method and a chamber useful for performing said method.

15 Claims, 11 Drawing Sheets

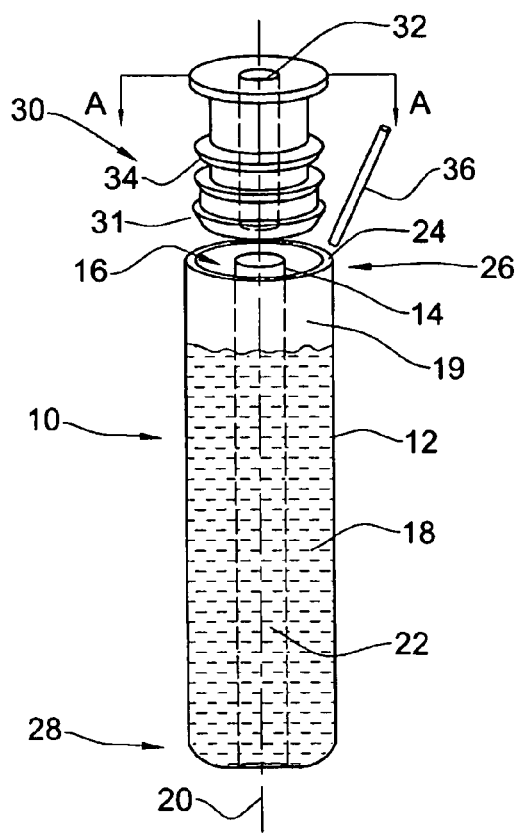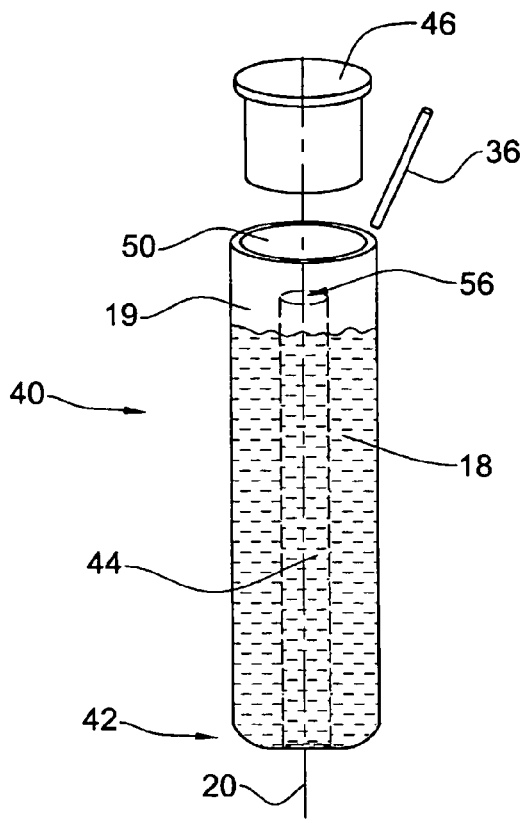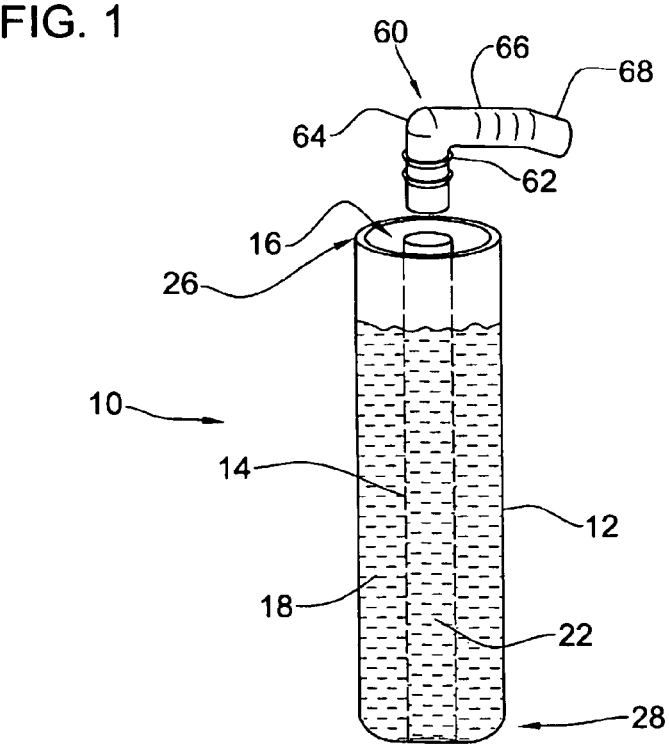

CHANGING THE TEMPERATURE OF A LIQUID SAMPLE AND A RECEPTACLE USEFUL THEREFOR

FIELD OF THE INVENTION

This invention relates to a method and apparatus for changing the temperature of a liquid sample, particularly the freezing and thawing of biological samples such as semen, and a receptacle useful therefor.

BACKGROUND OF THE INVENTION

Cryopreservation of cells, tissues and organs has vast implications on numerous procedures, for example grafting, in vitro manipulation (such as in vitro fertilization), research, etc. In a conventional slow-freezing method used for biological samples, a chamber is used in which the sample is introduced for freezing. Then, the temperature of the chamber is dropped in a controlled stepwise manner, thus exposing the sample to an external and gradual change in temperature.

A different technology for freezing is the "Multi-temperature gradient" (MTG) directional solidification, which is based on the invention disclosed in U.S. Pat. No. 5,873,254. In this technology, the sample is moved at a constant velocity (V) through temperature gradients (G) so the cooling rate (G×V) and ice front propagation are controlled and the velocity of the movement of the sample determines the morphology of the ice crystals formed within the sample. This method also enables the incorporation of controlled seeding into the freezing process.

The freezing of samples according to any of the known methods, even when using accurate freezing rate control systems, is typically adapted for small samples that are 5 milliliters or less in volume. This is partially due to the fact that, in large samples, some parts of the sample (usually the outer zone or part thereof) may chill or warm faster than other parts. Thus, freezing and storage of semen is performed regularly using mini (¼ cc) or midi (½ cc) straws. Samples with volumes of nearly 5 milliliters are usually frozen in plastic bags that are flattened during the preservation process, so as to have at least one dimension of the sample not exceeding 0.5 cm.

Solutions enabling freezing of larger samples have been suggested in co-pending PCT/IL02/00738 and PCT/IL03/00026. In the former application, a method is described wherein the sample is agitated during freezing under the directional solidification process. Thus, the rate of heat transfer within the sample is amplified, and the effect of the sample's bulk, morphology and heat transfer rate on the morphology of the forming ice crystals is reduced. In the latter application, an "isothermal-break" method is disclosed. In this method, the freezing or thawing of a sample is performed such that the sample is kept at a desired intermediate temperature at least for a time that would allow the temperature of the sample or a section thereof to become uniform and equal to the intermediate temperature.

SUMMARY OF THE INVENTION

The term "biological sample" means, in the present description and claims, an amount of biological matter including cells and/or group of cells and/or bodily fluids and/or any constituents thereof. For example, a sample may comprise semen, oocytes (ova), blood, blood cells, blood constituents, germ cells, umbilical cord blood, plasma, zygotes, embryos, etc.

The term "liquid sample" means, in the present description and claims, any sample which is essentially liquid but which may contain cells, cell parts, biological macromolecules, complexes of various substances, liposomes etc. Such sample may be derived from or contain a biological fluid (e.g. blood, semen, etc.). It may contain, in addition to or instead of the bodily fluid, also a non-biological liquid (e.g. a chemical solution). In fact, the term "liquid sample" is not limited to a biological sample and may comprise or consist of non-biological matter, for example, sensitive synthetic polymers.

One aspect of the present invention is connected with the use of a receptacle designed such that the surface/volume relation in a sample carried thereby is increased, whereby its ability to be uniformly frozen may be highly facilitated. This is achieved by an annular shape of the receptacle and, consequently, of the sample carried thereby, due to which the sample is free of a central core, the temperature of which would be the last to change especially if the sample has a large diameter. The annular receptacle may have other benefits in the cooling and warming of a liquid sample. One of which is that it may be cooled/or warmed both from the outside in and from the inside out.

The receptacle of the present invention has proximal and distal ends, an inner wall and an outer wall defining an annular portion therebetween adapted for receiving liquid therein, and an inner space defined by said inner wall. The inner wall may be open at each of said proximal and distal ends, enabling passage of fluid via said inner space whilst holding said liquid within said annular portion.

According to another aspect of the present invention, there is further provided a method for changing the temperature of a liquid sample, comprising:
(i) providing a receptacle having inner and outer walls defining an annular portion therebetween for receiving therein said liquid sample,
(ii) inserting said liquid sample, at a first temperature, into said annular portion, and
(iii) exposing said receptacle to a second temperature different from said first temperature.

When a biological sample containing living cells in a freezing solution is frozen, the first portion of the sample to freeze is the intercellular fluid. The formation of ice in the intercellular fluid increases the salt concentration therein. If the sample is frozen too slowly, the high concentration of salt in the intercellular fluid may kill the cells, by osmotic shock or by chemical toxicity. Conversely, freezing the sample too rapidly may lead to the formation of intracellular ice crystals, which also kill the cell, by internal mechanical damage. In addition, the rate of cooling affects the morphology of the intercellular ice crystals. Morphologies such as closely packed needles also kill cells, by external mechanical damage. Thus, maximizing the survival rate of cells subjected to freezing and thawing requires careful control of the freezing process.

In essence, any change in the temperature of a biological sample may damage it. Sperm, for example, may die or be injured such that after thawing of a frozen sperm sample there less live sperm will be observed and the surviving sperm may be less viable and/or less fertile than before they were subjected to the temperature change. However, as long as the "resultant quality" of the sample is such that the biological sample remains useful for a given purpose (e.g. cell line propagation, fertilization, grafting, infection, research purposes, etc.), the freezing and/or thawing are considered successful. Obviously, the higher the survival rate and the less the damage, the better is the method for changing the sample's temperature. However, each biological sample (depending on its purpose and composition) would have a "predetermined acceptable resultant quality" which is the worst quality of the biological sample after its temperature has been changed, that would still allow the sample to be useful. For example, in equine sperm under given circumstances, 35% post-thaw progressive linear motility (PLM; discussed below) is commonly considered a "passing" result, whereas less than 35% is considered "failing". Accordingly, the "predetermined acceptable resultant quality" may be that a desired number of the sperm samples would display, after having been frozen and thawed, 35% and higher progressive linear motility.

Thus, according to yet another aspect of the present invention a receptacle is provided for use in changing the temperature of a biological sample, said sample being characterized by a cross-sectional dimension along which the change of temperature may be performed with a predetermined acceptable resultant quality of the sample, said receptacle comprising an inner wall and an outer wall defining an annular portion therebetween for receiving said biological sample therein, said annular portion having a distance between said inner wall and said outer wall not exceeding said cross-sectional dimension of the sample.

In U.S. Pat. No. 4,140,489 to Lee, there is described a test tube having an annular portion, between the outer wall and inner wall constituted by an inverted inner tube, which is blocked at one end. The test tube is used for viewing microbial colonies, where a dark background can be inserted within the cavity of the inner tube to increase contrast, which clearly has nothing in common with the idea of the present invention.

As mentioned above, one of the benefits of having a receptacle with an annular portion in accordance with the present invention, is that the temperature of a liquid sample in such receptacle may be changed not only from the outside, but also from the inside, i.e. via the inner space surrounded by the annular portion.

Accordingly, the present invention further provides a chamber for facilitating changing the temperature of a liquid sample held within a receptacle, said receptacle comprising:
  proximal and distal ends;
  an inner wall and an outer wall defining an annular portion therebetween for receiving liquid therein; and
  an inner space defined by said inner wall open at each of said proximal and distal ends,
  said chamber comprising:
  a cavity for receiving said receptacle, and
  an inlet for inputting a heat transfer fluid into said cavity.

BRIEF DESCRIPTION OF THE DRAWINGS

In order to understand the invention and to see how it may be carried out in practice, some embodiments will now be described, by way of non-limiting examples only, with reference to the accompanying drawings, in which:

FIG. 1 is a perspective view of a receptacle and a plug according to one embodiment of the present invention;

FIG. 2 is a perspective view of a receptacle and a plug according to another embodiment of the present invention;

FIG. 3 is a perspective view of the receptacle of FIG. 1 with a conduit for facilitating the flow of a heat transfer fluid;

DETAILED DESCRIPTION OF THE INVENTION

Figure 4A:
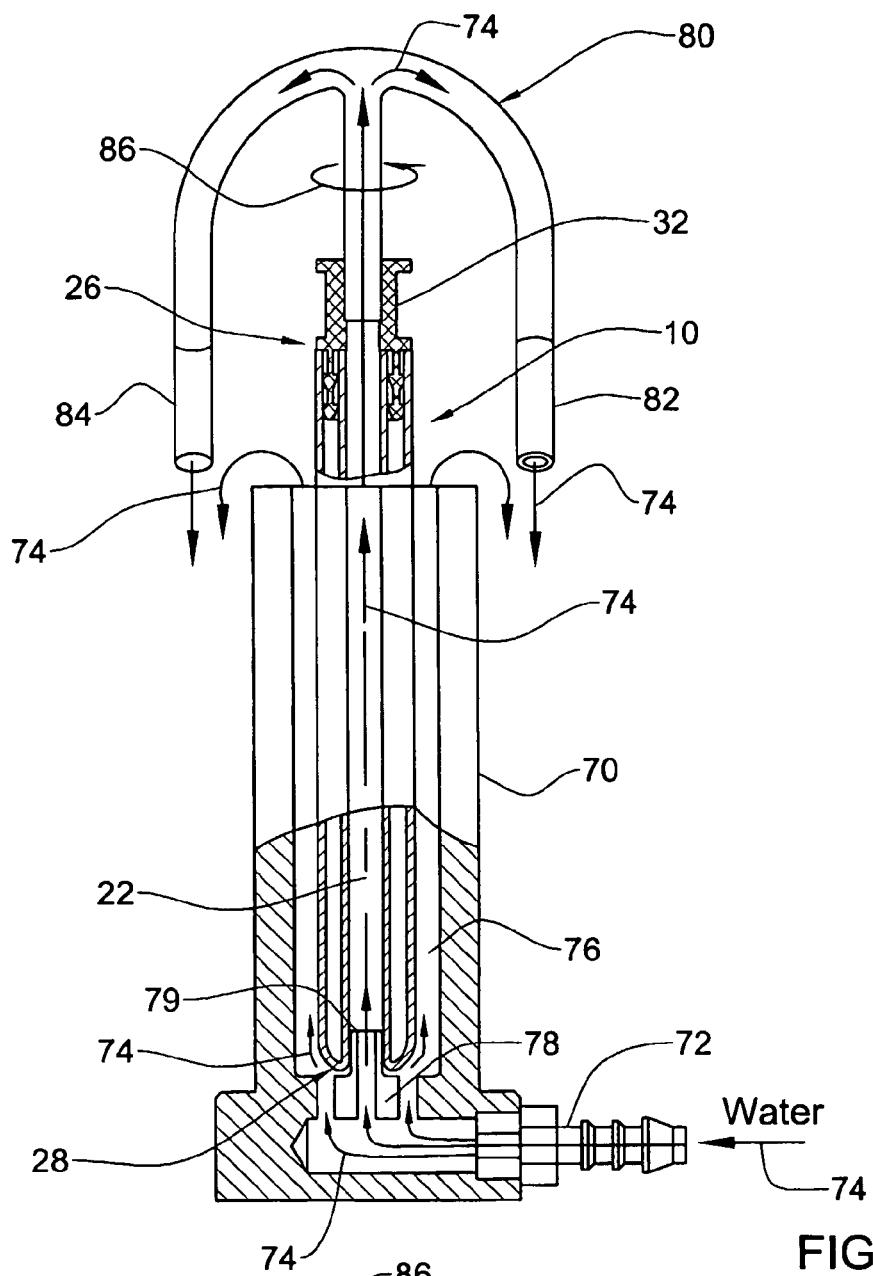
FIG. 4A is a partially cross-sectional view of a chamber according to the present invention with an inlet for facilitating the flow of a heat transfer fluid, and with a receptacle and plug as in FIG. 1 received therein.

Referring first to FIG. 1 of the drawings, there is shown a test-tube like receptacle 10 comprising an outer wall 12 and an inner wall 14 defining therebetween an annular portion 16 within which a liquid 18 may be received. A longitudinal axis 20 extends through the center of an inner space 22 defined by the inner wall 14 of the receptacle 10. The annular portion 16 has an opening 24 at a proximal end 26 of the receptacle 10 and is sealed at a distal end 28.

It should be noted that the geometry of the receptacle 10 is advantageous in both the rate of heating/cooling of the liquid 18, as well as the uniformity of the temperature during the heating/cooling process, in that it provides a reduced heat transfer path as compared to a receptacle such as a standard test tube of similar outer dimensions. The receptacle may be manufactured from any material that would allow heat transfer to and from the sample, and that would withstand the temperatures changes to which it is subjected, including glass, metal and various polymers, etc. The receptacle has an essentially circular cross-section taken perpendicularly to the longitudinal axis, however, the present invention is not limited to such cross-section. Other possible cross-sections may be square, rectangular, octagonal, and even irregular. Naturally, the stoppers used with the various shapes of cross-section would need to have a sealing portion compatible with that of the receptacle.

Figure 6:
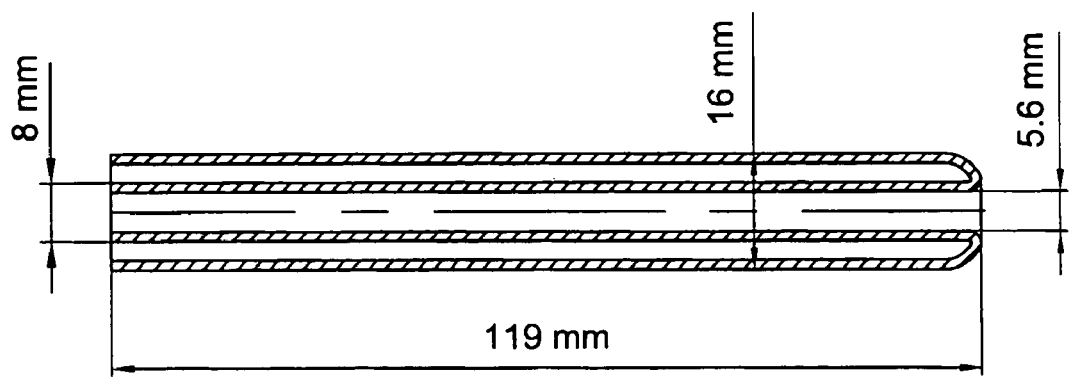
FIG. 6 is a cross-sectional view along the line A-A, of a receptacle of the present invention, similar to that shown in FIG. 1, with the indication of examples of dimensions of such receptacle.

The outer and inner walls 12 and 14 provide increased heat transfer surface to the receptacle 10. The inner space 22 may be open at both the distal end 28 and proximal end 26 of the receptacle as shown in FIG. 6, in which case a heat transfer fluid may flow into and through the inner space in from the distal end 28 and out via the proximal end 26, or vice versa, without entering the annular portion 16.

It is appreciated that in some cases it may be useful or necessary to seal the proximal end 26 of the receptacle 10, so that matter may not exit and or enter the annular portion 16, such as when contaminants are to be kept out, to protect a handler and surroundings, to prevent spillage and loss of possibly valuable liquid, etc.

One means for sealing the proximal end 26 of the annular portion 16 is a plug 30 (FIG. 1), which has a bore 32 corresponding to and aligned with the inner space 22 of the receptacle 10. Accordingly, the part of the plug 30 surrounding the bore 32 has an annular sealing portion 31 corresponding to the proximal end 26 of the annular portion 16. The configuration of plug 30 is useful especially when heat transfer fluid, used to warm or cool the liquid sample, is arranged to flow through inner space 22. In such case the heat transfer fluid may flow in and out of the proximal end 26 of inner space 22 via bore 32 without entering the annular portion 16 wherein the liquid sample is located.

The plug 30 further comprises flexible ribs 34 for providing proper sealing of the receptacle 10—although the plug itself may be made of a flexible/resilient material for providing a proper seal without the need for ribs.

Further seen in FIG. 1 is a wand 36 associated with the plug 30. Such wand 36 may be an integral, removable part of plug 30 or merely in close association thereto. Upon inserting the plug 30 into the receptacle 10, the wand 36 is placed at the periphery of the plug. This provides an escape for air 19 from the annular portion 16 that would otherwise be compressed upon sealing with the plug 30. The wand 36 can be removed after plug 30 has been inserted, thus ensuring that the annular portion 16 of the receptacle 10 is sealed. The escape of air 19 reduces the pressure in the annular portion 16 thus reducing the chance for mechanical failure of the receptacle 10, particularly upon exposure to temperature change.

Further embodiments are illustrated with reference to FIGS. 2-4. For the sake of clarity, similar parts in various embodiments of the present invention described hereinafter will be designated with the same reference numerals.

In contrast to the receptacle 10 of FIG. 1, FIG. 2 shows a receptacle 40, where an inner space 44 of the receptacle is sealed at the proximal end 56 of the receptacle. This configuration precludes the option of flowing a heat transfer fluid in via one end of the inner space 44 and out the other (sealed) end. However, this may result in a somewhat sturdier receptacle. Still, the heat transfer fluid could flow in and back out of the distal end 42, thereby improving heat transfer.

In FIG. 2 plug 46 is shown that is different from the plug 30 (FIG. 1) in that it does not have a bore 32. It should be understood that the plug 30 shown in FIG. 1 could be used with the receptacle 40 shown in FIG. 2, and vice versa, as well as plugs and receptacles of other designs. For example—the receptacle may be sealed by an external stopper that need not be inserted into the proximal end 26. A plugging member could be screwed onto the receptacle according to the invention, provided that the receptacle is adapted accordingly at its proximal end 26. In fact, the annular portion of the tube may be simply sealed with a firmly attached (e.g. glued) cover.

FIG. 3 shows the receptacle 10 associated with a generally L-shaped conduit 60 comprising a leg 62 correspondingly aligned with, and for inserting into, the inner space 22 of the receptacle. The leg 62 is designed to be received within the inner space 22 of the receptacle 10 at its proximal end 26, such that the exit of fluid from said proximal end 26 of the inner space 22 would be only through the conduit 60. Thus, conduit 60 may be equipped with ribs 64 for improved sealing. Extending from the leg 62 is an arm 66, which is shown comprising a downwardly directed portion 68.

This arrangement facilitates the cooling/heating of the liquid 18, as a heat transfer fluid can then flow into and through the inner space 22 and out the conduit 60 via arm 66, or vice versa, similarly to the arrangement shown in FIG. 1 wherein the plug 30 has a bore 32.

The conduit 60 is sufficient to preclude heat transfer fluid from entering the annular portion 16 without the use of a plug, however a plug is useful especially in the case where the liquid 18 is a biological liquid, or any other liquid wherein it is important to keep contaminants out, etc. The use of a plug with a bore, such as plug 30 comprising bore 32, allows the use of a conduit in conjunction with the plug, the utility of which will be further understood from the description associated with FIGS. 4A and 4B.

FIG. 4A shows a cross-section of a heat transfer chamber 70 having an inlet 72 for water or other heat transfer fluid (which can comprise a liquid, gas or mixture thereof) represented by and flowing as shown by arrows 74. The chamber 70 further comprises a cavity 76, designed for receiving the receptacle 10, and, at the bottom of the cavity, a manifold 78, for distributing the water around and through the receptacle 10. It is appreciated that a manifold may distribute the liquid around the receptacle more evenly than would a single outlet, but the invention is not limited to having a manifold in the chamber. Additionally, there may be more than one outlet and/or inlet, and the heat transfer fluid may flow into the chamber from more than location.

Figure 4B:
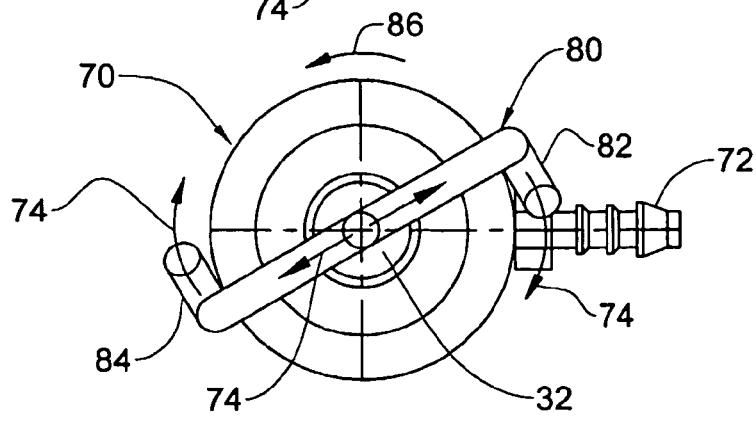
FIG. 4B is a top view of the chamber of FIG. 4A.

The plug 30 is shown sealingly inserted in the proximal end 26 of the receptacle 10. A conduit 80 is also shown, being a combination of a T-shape and an inverted U-shape, sealingly inserted in the bore 32 of plug 30. The conduit 80 comprises extensions 82 and 84 that are directed in opposing directions and are perpendicular to the conduit when viewed from above (FIG. 4B). Thus, when the water flows in the direction of arrows 74, the receptacle 10 will spin in a direction as shown by arrow 86. This spinning will have the effect of mixing the liquid 18 and thereby improving the uniformity of its temperature. The spinning may also improve the heat transfer rate by imparting an aspect of turbulence to the heat transfer fluid. The present invention is not limited to the shapes of conduits 60 and 80, and conduits of countless other shapes may perform functions similar to those described.

The chamber 70 further comprises as part of manifold 78, a protrusion 79 protruding partially into the distal end 28 of the inner space 22. This protrusion 79 facilitates a portion of heat transfer fluid (represented by arrows 74) to be directed into the inner space 22 and at the same time serves to position the receptacle 10 within chamber 70.

One of the useful applications of a receptacle according to the invention is in the cryopreservation of biological samples. As discussed above, since biological samples are sensitive to freezing and thawing, it is preferred to freeze and thaw all parts of a biological sample essentially uniformly, and as close as possible to the optimal rate.

According to one aspect of the present invention, the temperature of a liquid sample in a receptacle such as receptacle 10 in FIG. 1 is changed as follows. Liquid 18 at a given temperature is first inserted into the annular portion 16 of the receptacle 10 which is then sealed with the plug 32, 46. Alternatively, the inner space 22 is sealed with a conduit 60, 80 or by a combination of plug 32 and a conduit. The receptacle 10 containing the liquid 18 is then exposed to a temperature different from the given temperature of the sample. This is accomplished by placing the receptacle 10 in the chamber 70 and flowing a heat transfer fluid, such as water through and around the receptacle. The chamber 70 can be located in a water bath 90 (see FIG. 5) whose temperature is controllable by any temperature control and monitoring system exemplified by system 92. System 92 may also comprise a pump for pumping water into chamber 70 into inlet 72.

Alternatively, and especially in the case where the liquid 18 is a biological sample, other methods for freezing the liquid sample in the receptacle 10 can be used, such as movement of the receptacle through an environment with a temperature gradient in a given direction with the longitudinal axis 20 of the receptacle being essentially parallel to that direction. Other methods are disclosed in U.S. Pat. No. 5,873,254 and in co-pending PCT Application No. PCT/IL03/00026. The receptacle 10 may also be agitated during its movement along the gradient, as described in co-pending PCT Application No. PCT/IL02/00738. Alternatively, the liquid 18 can be frozen or thawed and brought to a 'final' desired temperature using the chamber 70 as just described.

Freezing

The process of freezing a liquid sample (5% Ethylene Glycol in water) in a receptacle such as receptacle 10 having the dimensions shown in FIG. 6 was compared with a regular or "control" tube. The chamber was of the configuration shown in FIG. 4. The control tube was a conventional laboratory test tube, 10 cm long with an outer diameter of 1.6 cm (ASSISTENT™, Germany). Both the receptacle and the control tube were made of glass.

The tube and the receptacle were each filled the liquid and two thermocouples (TCs) (ALMEMO$^R$ 2290-4) were inserted into each. In the control tube the "outer" TC was situated adjacent to the outer wall of the tube and the "inner" TC was situated in the midst of the liquid. In the receptacle, the "outer" TC was situated adjacent to the outer wall of the tube and the "inner" TC was adjacent to the inner wall of the tube. The tube and receptacle were each plugged with silicon rubber stoppers such as plug 32 of FIG. 4A. The tube and the receptacle were each frozen by dropping into liquid nitrogen and the temperatures were measured throughout the freezing process using the TCs.

Figure 7A:
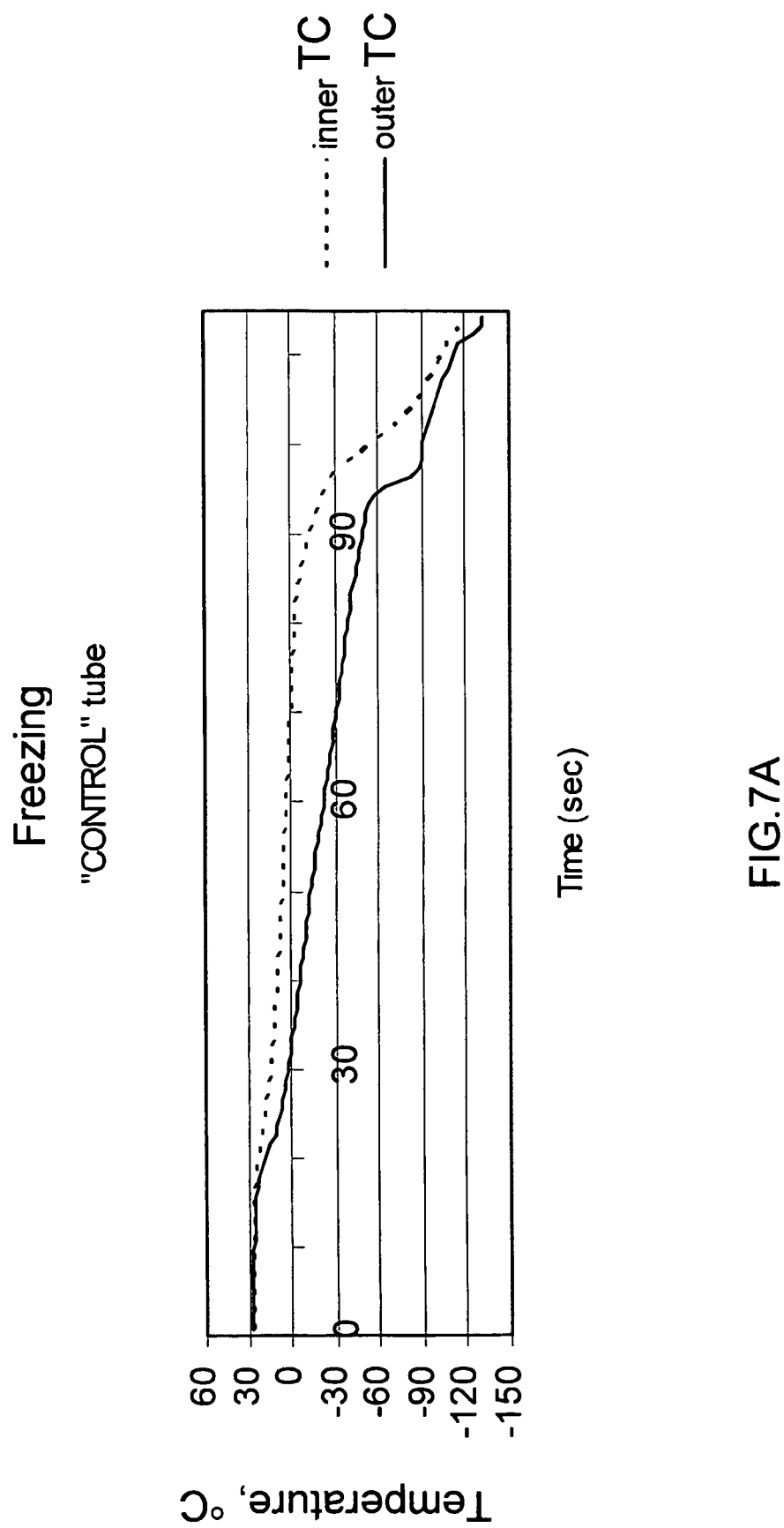
FIG. 7A is a graphical representation of the temperatures measured during freezing at an inner (mid-point) position and an outer (wall) position of a liquid sample in a conventional test tube.
Figure 7B:
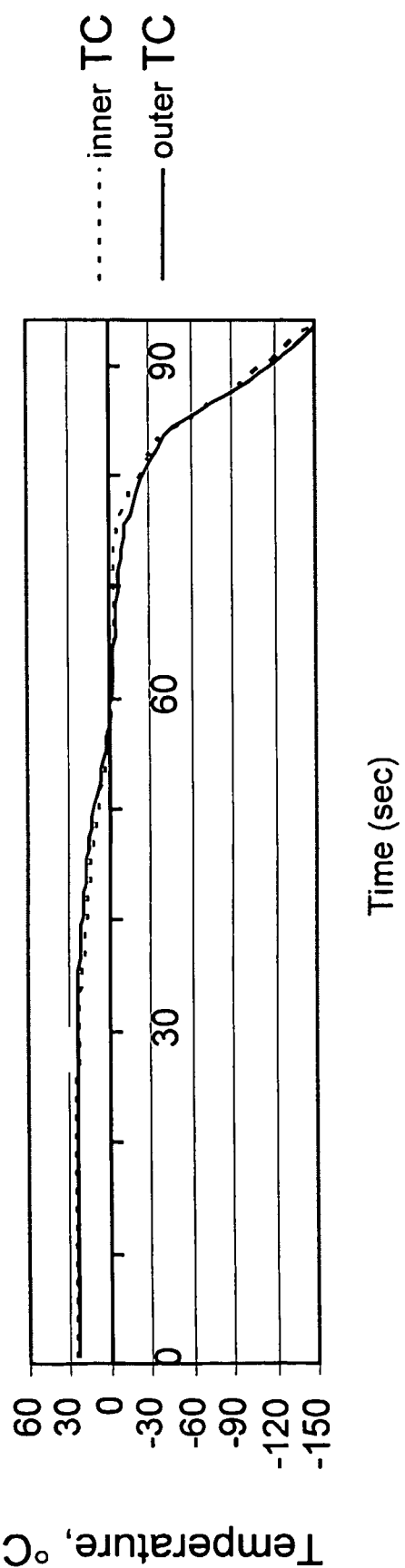
FIG. 7B is a graphical representation of the temperatures measured during freezing at an inner (mid-point) position and an outer (wall) position of a liquid frozen in a receptacle such as shown in FIG. 1.

As seen in FIG. 7A, in the control tube there was a difference between the rate of freezing measured by the inner TC and that measured by the outer TC. In contrast, in the receptacle the rates of freezing measured by the inner and outer TCs were very similar, as seen in FIG. 7B.

Thawing:

The process of thawing a liquid sample in a receptacle such as that shown in FIG. 6 was also compared with a conventional "control" tube. The tube, receptacle, liquid, plugs and TCs were the same as described above for the freezing experiment, the only difference being that just one TC was inserted into each, at a mid-point of the liquid. In the receptacle this mid-point was in the annular portion, between the inner and outer walls.

Figure 5:
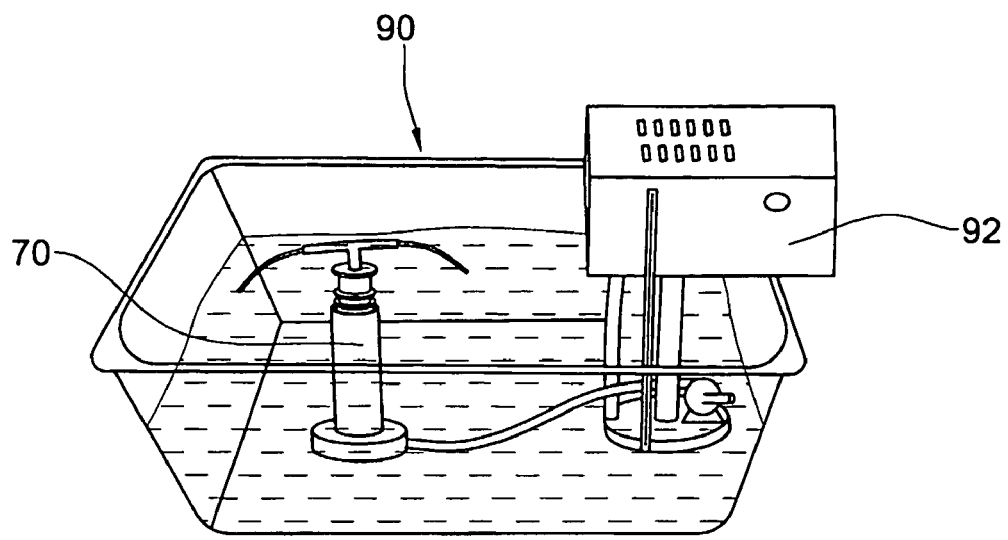
FIG. 5 is a schematic illustration of one example of use of the chamber shown in FIG. 4A.

The thawing process commenced by removing both tubes from liquid nitrogen and placing at room temperature. After 1 minute and 30 seconds, when the temperature of the liquid in both cases was approximately −100° C., the tube and the receptacle were transferred into a copper chamber (analogous to chamber 70 of FIG. 4A) located in a conventional water bath (as shown in FIG. 5) that was kept at a temperature of 37° C.

The control (conventional) tube and a first receptacle were essentially motionless within the chamber during thawing, with no water flowing over the tubes. A second receptacle was inserted into the chamber, and water from the water bath was pumped through the inner space of the second receptacle at a rate of 500 ml per minute.

Figure 8:
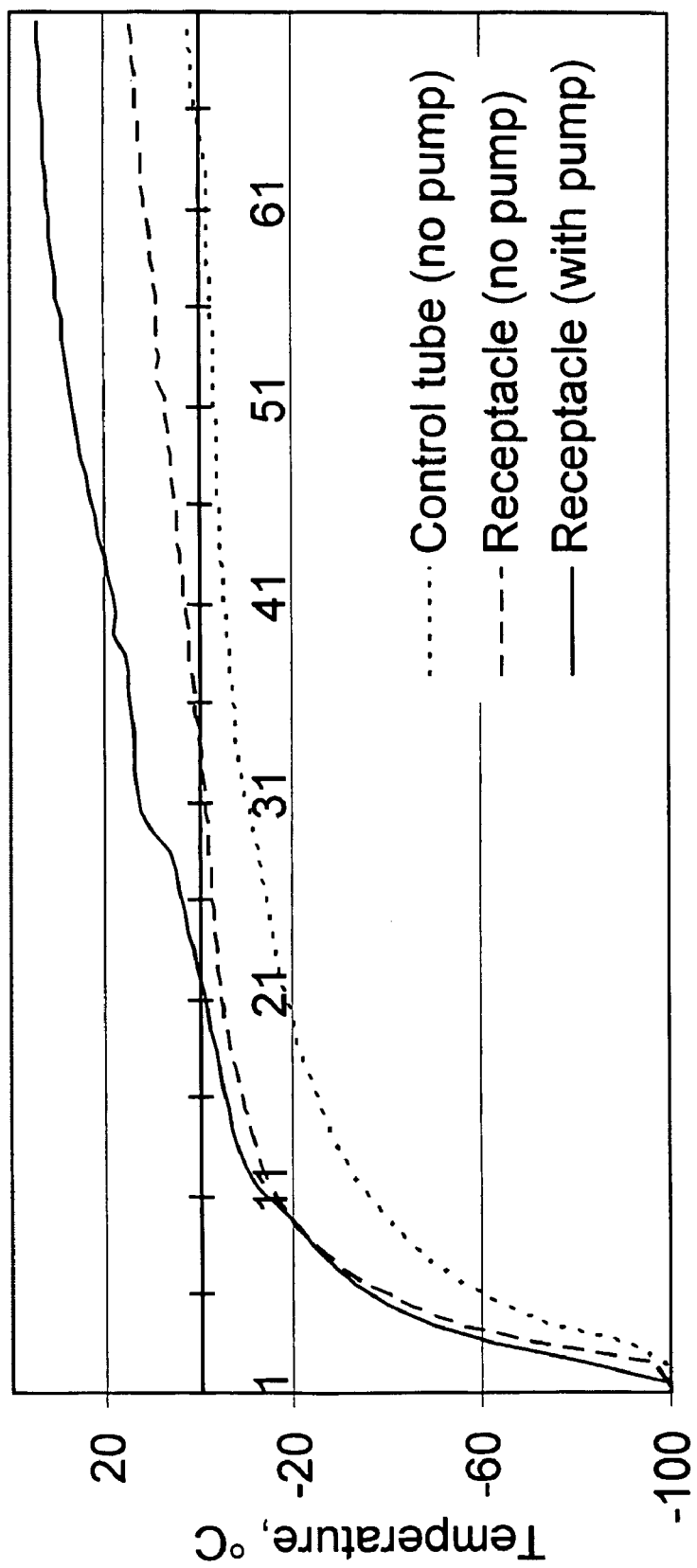
FIG. 8 is a graphical representation of the temperatures measured during thawing at an inner (mid-point) position of a conventional tube and the receptacle of FIG. 6, with and without pumping water into the chamber during thawing.

The temperatures measured during thawing in the bath are shown in FIG. 8. The thawing rate of the first receptacle in the conventional bath was faster than that of the control (conventional) tube. The fastest thawing rate was observed with the second receptacle. This improvement was obtained in this example without rotation of the receptacle during thawing.

Freezing and Thawing of Equine Sperm

Equine (horse) semen was frozen according to one embodiment of the present invention. A total of 97 ejaculates were collected from 31 different stallions using a Missouri model artificial vagina with an in-line filter to remove the gel fraction of semen. Each ejaculate was immediately diluted 1:1 with a conventional synthetic centrifuge medium (sorbitol extender) pre-warmed to 37° C. The solution was centrifuged at 1000×G for 25 minutes in 50 ml centrifuge tubes containing 2 ml of the density medium iodixanol to reduce sperm damage and increase sperm recovery.

The resulting sperm was harvested using stainless steel cannulae, and was split into two halves. One half was diluted to $150 \times 10^6$ sperm/ml and the other half was diluted to $60 \times 10^6$ sperm/ml with 20% egg yolk glucose/lactose/EDTA freezing extender.

The semen diluted to $150 \times 10^6$ sperm/ml was packaged into 0.5 ml plastic straws. Semen diluted to $60 \times 10^6$ sperm/ml was packaged into 10 ml receptacles of the shape and dimensions depicted in FIG. 6, with silicon rubber stoppers such as plug 32 of FIG. 4A. Straws and receptacles containing the semen were then placed into a refrigerator at 4° C. and chilled for approximately 2 hours.

Straws were frozen in a conventional Planer™ cell freezer (pre-programmable liquid nitrogen vapor freezing device, Planer, UK and programmed with a standard equine freezing curve (IMV, France). The straws were then plunged into liquid nitrogen.

The receptacles were frozen in a model MTG516 freezing device (Interface Multigrad Technology, Israel). The initial temperature was 5° C. and the final temperature was −50° C.; the receptacles being moved through the MTG516 device at a speed of 1.0 mm/sec. Seeding (freezing nucleation) was done automatically for 60 seconds. The receptacles were then plunged into liquid nitrogen.

For thawing, the straws were plunged into a water bath at 37° C. for 30 seconds and then removed and dried thoroughly with paper towels. After drying the seal was cut opened at one end and the contents were transferred into a pre-warmed 4 ml plastic tube.

Receptacles were thawed by removing them from the liquid nitrogen and allowing them to stand in air at room temperature for 1 minute 30 seconds. After this time they were placed into a chamber such as depicted in FIGS. 4A and 4B, at 37° C. for 30 seconds with water pumped at a rate of 500 ml per minute. The receptacle was removed and dried thoroughly with a paper towel. After drying, the plug was removed and a sample of semen was transferred into a pre-warmed 4 ml plastic tube.

Post-thaw Evaluation:

A comparison was made between the two treatment groups by evaluating the sperm in vitro according to the following laboratory techniques:

Progressive Linear Motility (PLM)

Sperm were examined under phase contrast microscopy and an estimation of the percentage of sperm progressing in a substantially straight line was made and recorded. Although subjective, this test is considered the industry standard at present.

Osmotic Resistance Test (ORT)

This test partially mimics the stress exerted on sperm after insemination by incubating them in a hypotonic solution prior to staining them with a fluorescent dye that illuminates sperm intolerant of this stress. Sperm were then counted to compare a live/dead ratio.

Acridine Orange/Propidium Iodide Dual Fluorescence Test (AO/PI)

Using these two fluorescent chemicals in combination, the membrane integrity of the sperm was examined and a live/dead ratio was calculated (live sperm fluoresce green and dead sperm fluoresce red).

Pass/Fail Criteria

Sperm that exhibited sperm motility below 35% were considered sub-standard (failing). This population would typically fail an examination and would not be used for insemination. Accordingly, sperm that exhibited sperm motility above 35% were considered to have passed.

Results

As mentioned a total number of 97 ejaculates from 31 stallions were tested. The proportions of the sperm that passed the motility tests were 57/97 (59%) for sperm frozen in straws (Planer freeze) and 85/97 (88%) for sperm frozen in receptacles. As a control, semen from 41 ejaculates was kept unfrozen and was tested after being chilled at 5° C. for 30 hours.

Of the 97 ejaculates, only 9 (9%) produced a failing result regardless whether they were frozen in straws or receptacles (Fail-Fail group), 30 (31%) failed after having been frozen in straws but passed when frozen in receptacles (Fail-Pass group) and 55 (57%) passed regardless of whether they were frozen in a straw or receptacle (Pass-Pass group). Only 3% (3 ejaculates) failed when having been frozen in a receptacle but passed when having been frozen in straws (Pass-Fail group).

Figure 10A:
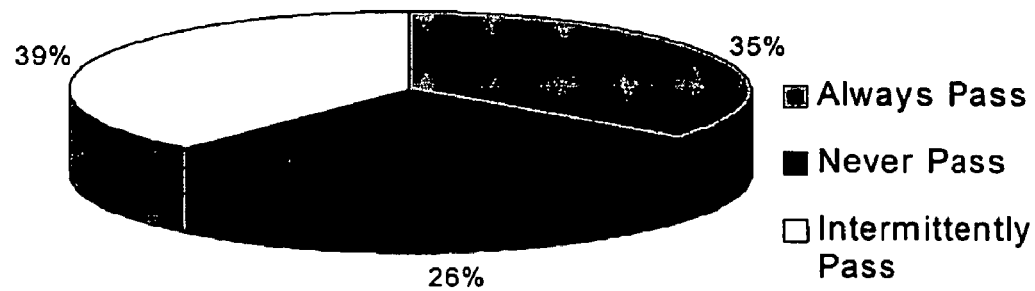
FIG. 10A is a pie chart showing the rates of failing and passing in the progressive linear motility (PLM) tests for different stallions after having their sperm frozen in straws.
Figure 10B:
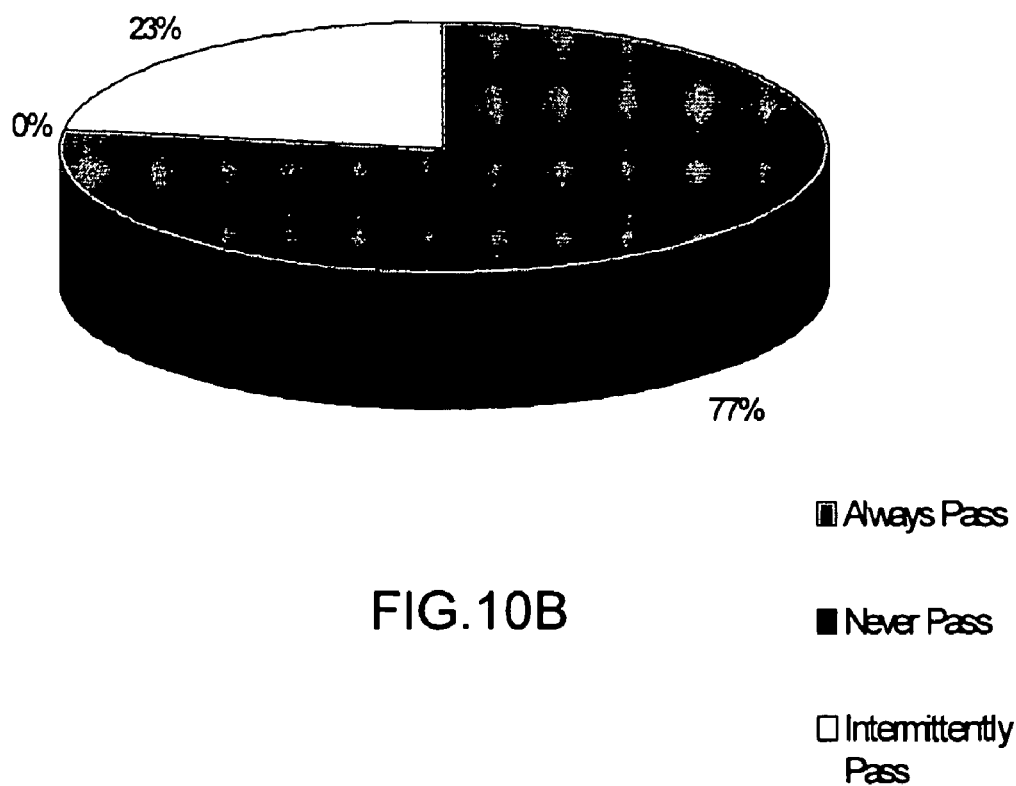
FIG. 10B is a pie chart showing the rates of failing and passing in the progressive linear motility (PLM) tests for different stallions after having their sperm frozen in receptacles as shown in FIG. 6.
Figure 11A:
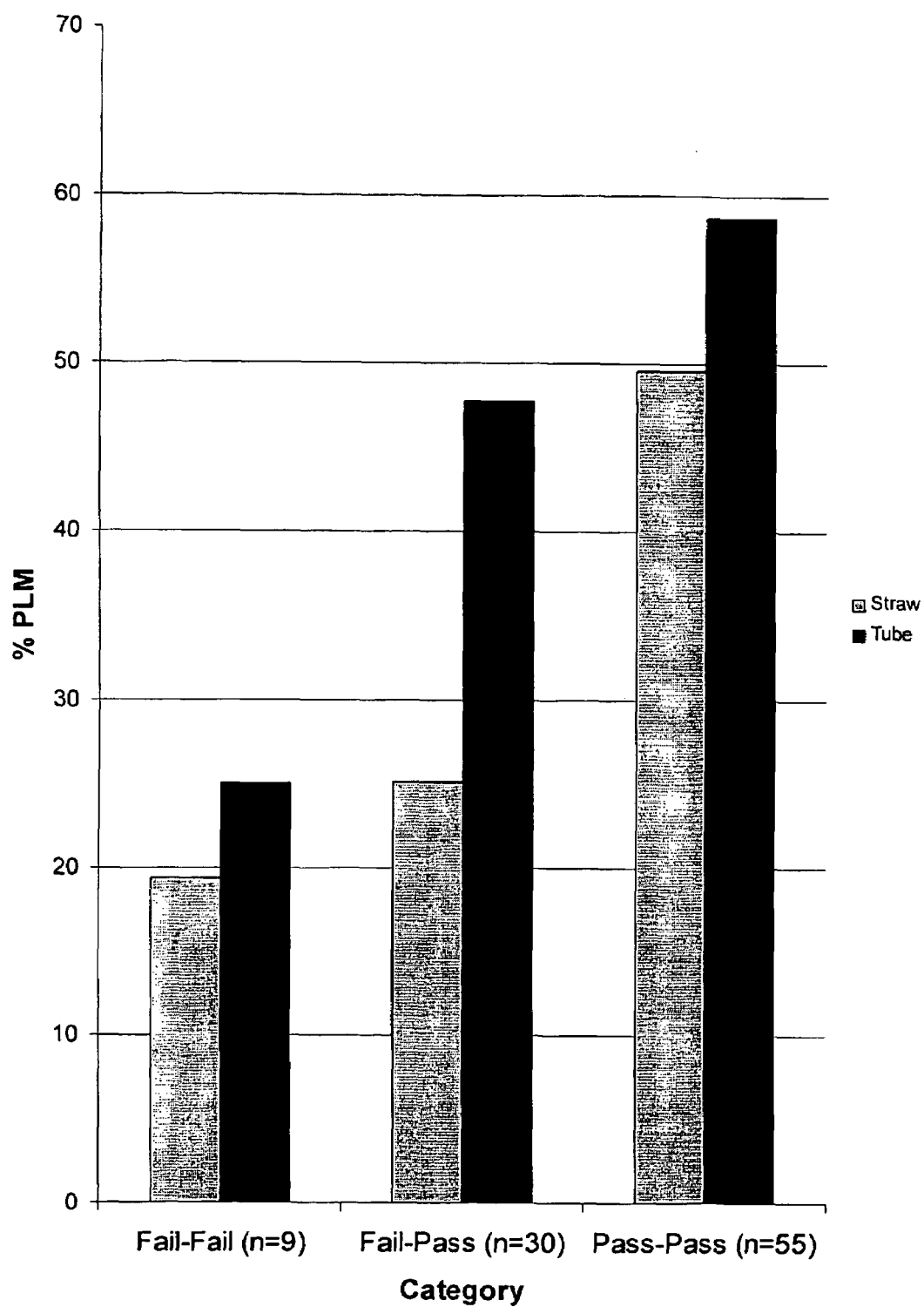
FIG. 11A relates to the progressive linear motility of the sperm, FIG. 11B relates the percent of live cells according to an AO/PI assay, and FIG. 11C relates the percent of live cells according to an ORT assay.
Figure 11B:
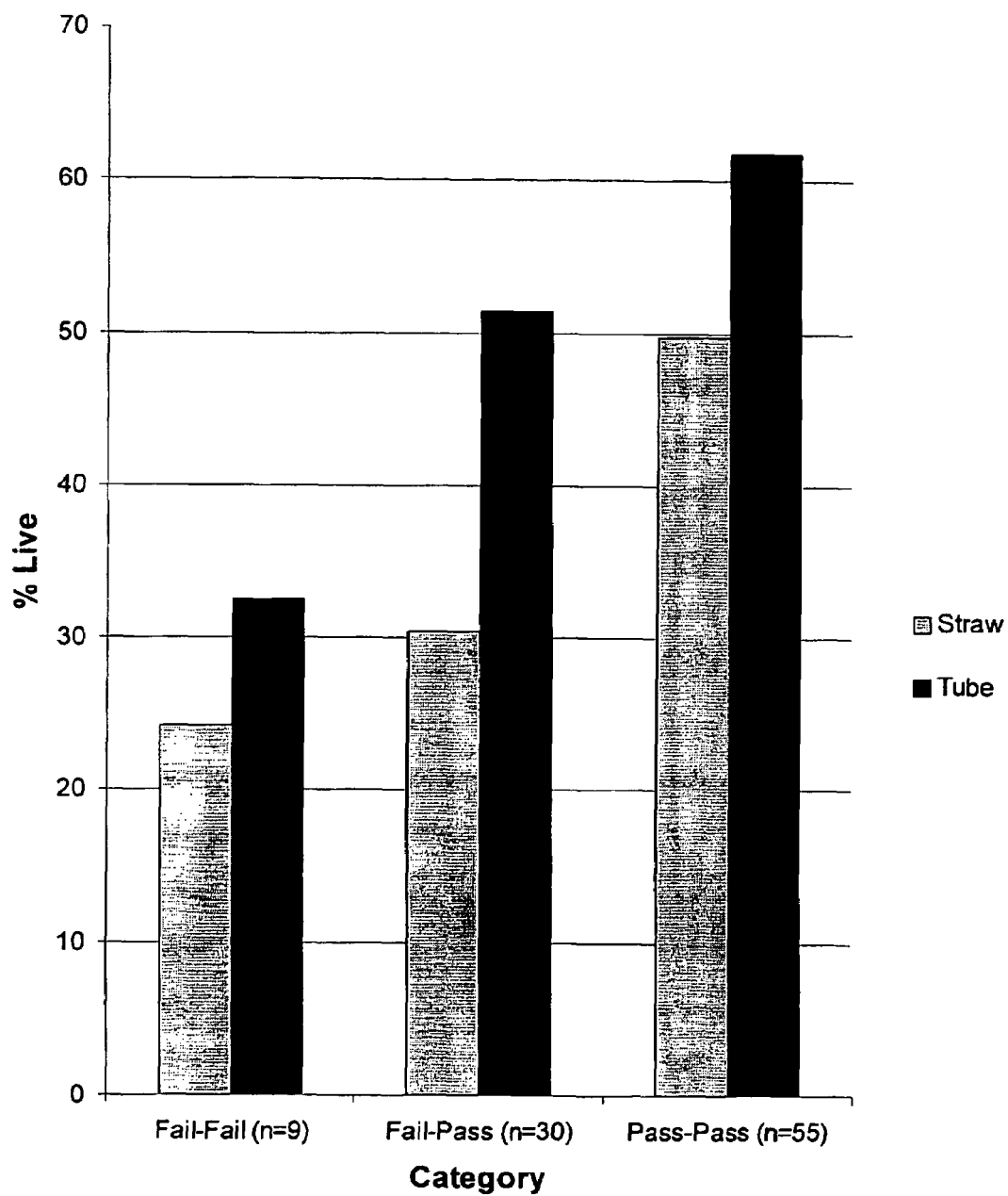
FIG. 11 is a comparison of the post-thaw parameters measured for sperm that was frozen and thawed either in a straw or in a receptacle as shown in FIG. 6. The results are grouped according to its failing or passing of the progressive linear motility (PLM) test after thawing where.
Figure 11C:
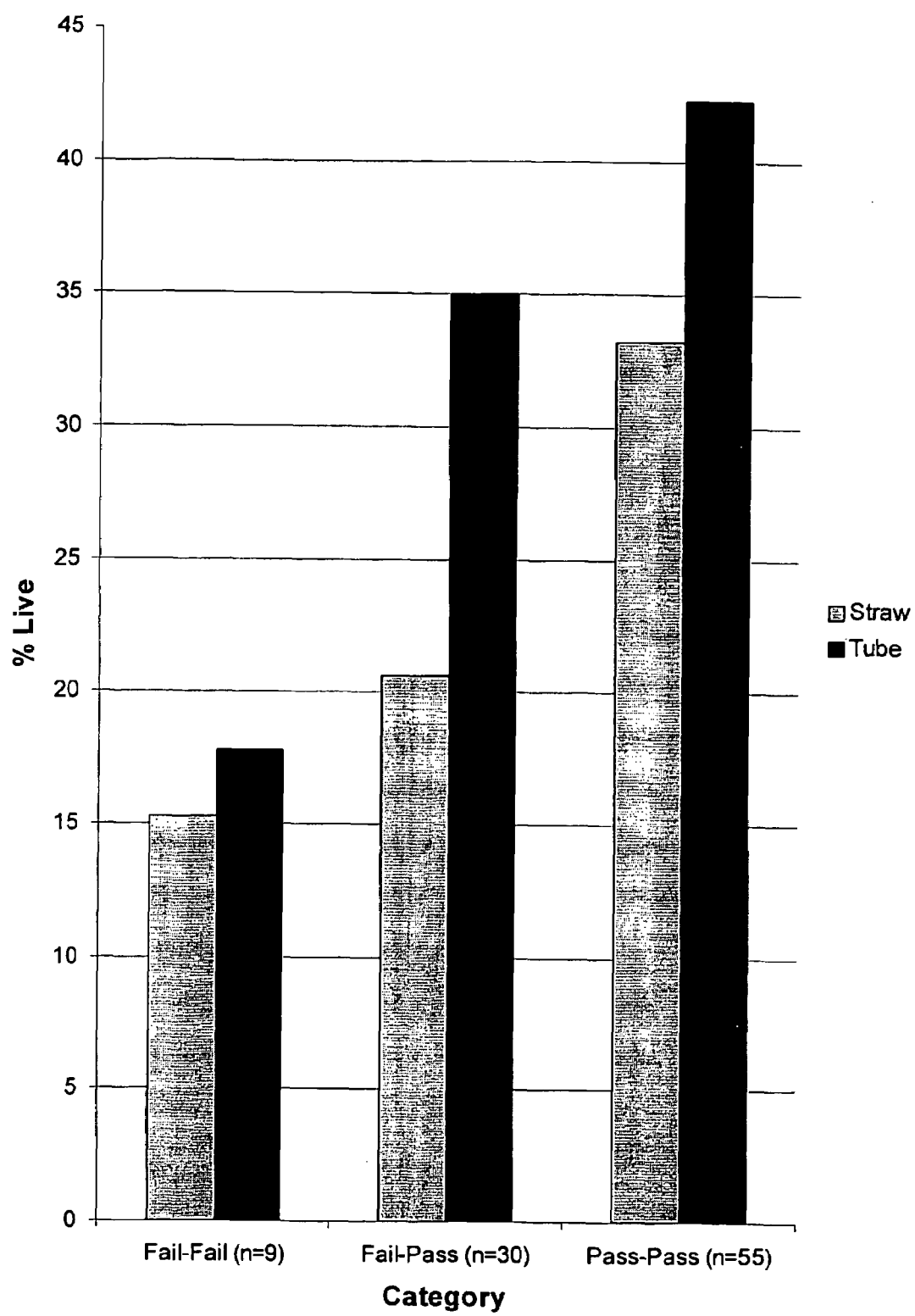

Of the 31 stallions, the following results were observed: When frozen in straws—the semen of 11 stallions (35%) always passed, 8 (26%) never passed, and 12 (39%) sometimes failed and sometimes passed (intermittently pass). These results are illustrated in a pie chart in FIG. 10A. When frozen in receptacles, the semen of 24 stallions (77%) always passed and 7 (23%) intermittently passed. None of the stallions' semen always failed after cryopreservation in receptacles. These results are shown in a pie chart in FIG. 10B. The results of the cryopreservation of the stallion semen are differently detailed in Table I.

TABLE I

| Category | Straws | | | Tubes | | |
|---|---|---|---|---|---|---|
| | PLM (%) | AO/PI (% live) | ORT (% live) | PLM (%) | AO/PI (% live) | ORT (% live) |
| Fail-Fail (n = 9) | 19.4 | 24.2 | 15.3 | 25.0 | 32.5 | 17.8 |
| Fail-Pass (n = 30) | 25.1 | 30.4 | 20.6 | 47.8 | 51.4 | 35.0 |
| Pass-Pass (n = 55) | 49.6 | 49.7 | 33.2 | 58.7 | 61.8 | 42.3 |
| Pass-Fail (n = 3) | 35.0 | 26.0 | 17.6 | 18.3 | 35.9 | 24.8 |
| Total (n = 97) | 37.4 | 39.5 | 26.5 | 50.2 | 53.6 | 36.2 |

For comparison, semen that was chilled for 30 hours, gave the following average results: 55.9% motility (n=41), 57.9% live AO/PI (n=41) and 46.5% live ORT (n=35). The average results of the sperm that were frozen in straws, frozen in receptacles or kept chilled without freezing are summarized in Table II.

TABLE II

| Sperm treatment | PLM (%) | AO/PI (% live) | ORT (% live) |
|---|---|---|---|
| Chilled semen | 55.9 | 57.9 | 46.5 |
| Planer Straw (frozen) | 37.4 | 39.5 | 26.5 |
| Receptacle (frozen) | 50.2 | 53.6 | 36.2 |

Figure 9:
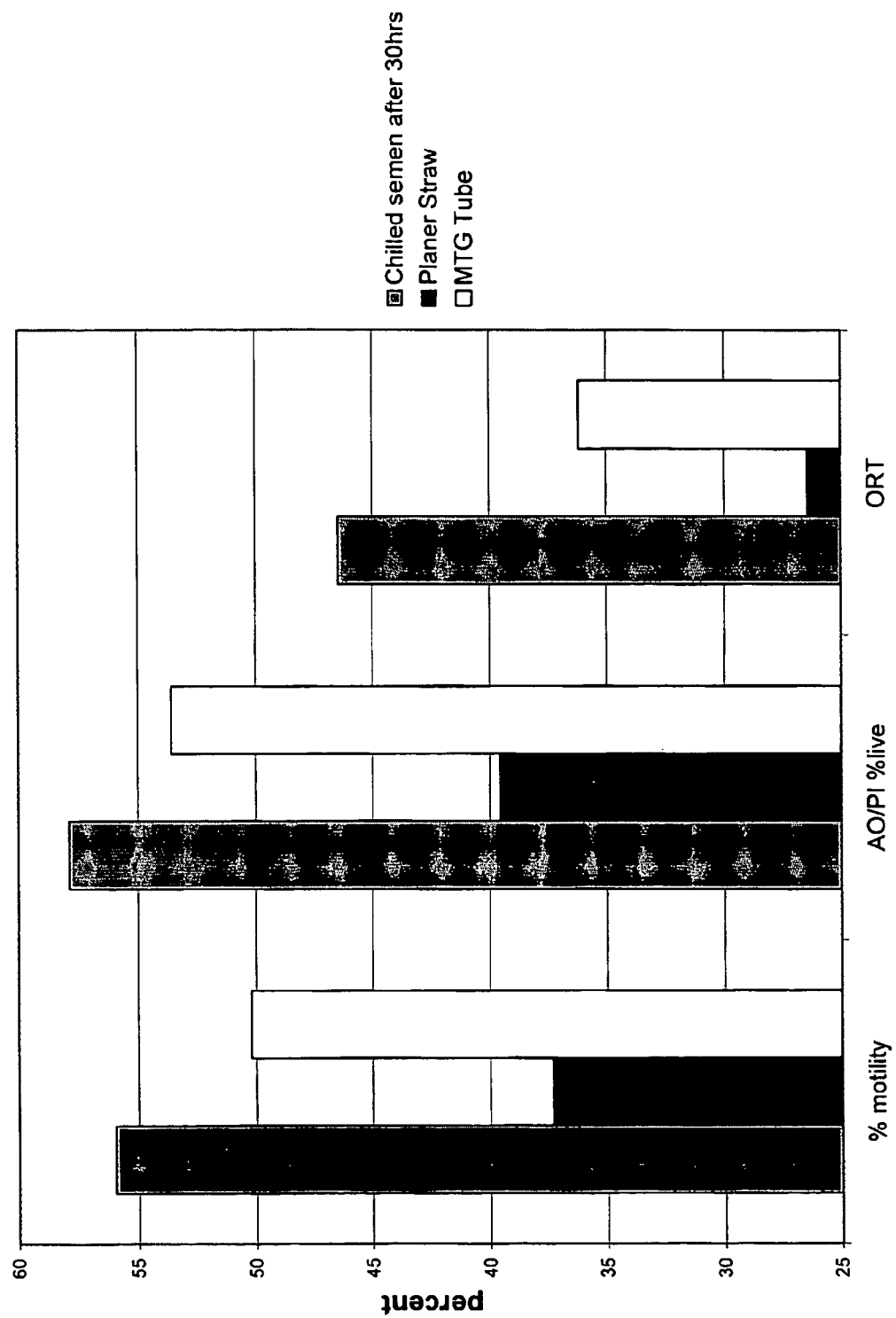
FIG. 9 is a column chart comparing the viability and motility parameters measured for equine semen after one of the following: (a) being chilled for 30 hours, (b) being frozen in a straw using a Planer freezing apparatus or (c) being frozen in a receptacle as shown in FIG. 6.

As seen in Table II and FIG. 9, on average, the best results were obtained by the chilled semen. However, chilled semen cannot be stored for the same duration as frozen sperm. Also seen, the sperm frozen using the receptacles displayed comparable results to those of the chilled semen both in the motility assay (PLM) and in the AO/PI staining. In all experiments the semen frozen using the receptacles gave better results than that of the straws. Some of the advantages of the present invention may include the large surface area of the receptacle for contact with heat transfer fluid—or with other heat conducting arrangements—and the improved rate and uniformity of the temperature change due to the large surface area/volume ratio.

In the sport horse breeding industry (show jumping, eventing, dressage, etc), artificial insemination using chilled semen is the preferred medium to work with over natural service. The method and apparatus of the present invention may allow the production of frozen semen that shares the benefits of chilled and conventionally frozen semen with reduced disadvantages as compared with the conventional freezing in straws.

While the above measurements and analyses were related to the freezing and thawing of equine semen, it should be understood that the results are indicative of results for many other liquid samples and the method and apparatus disclosed are applicable not only to other semen and biological samples, rather also to a variety of liquid samples wherein the controlled heating and/or cooling of a liquid is desired.

It should also be noted that the method and various components of the present invention described above, as well as variations thereof, are provided merely by way of illustration and are by no means exclusive, and many variations and modifications are possible.

For example, several alternatives may be used regarding the wand 36 to release the air 19, which is compressed when the plug 30 or 46 is inserted into the receptacle 10 or 40. One option is the insertion of an object such as a needle to allow the air to exit and then removal of the object to allow the plug to seal the receptacle 10 or 40. Alternatively, the plug may comprise, for example, one or more channels for performing same with diameters and/or tortuous paths so as to prevent contamination. Also, the ribs 34 that are first inserted into the receptacle 10 or 40 may in themselves have rigid projections to allow the air to exit while the plug 30 46 is inserted. In such case the last rings 34 would then seal the receptacle 10 or 40, as the plug is further inserted. In another example, the plug 30 or 46 could comprise ribs (or concave annular channels) on an inner wall thereof (where the plug's inner wall contacts the outer surface of the receptacle's inner wall 14) in order to ensure sealing of the annular portion 16.

In still another example, the conduit 60 or 80 can be of various configurations in addition to T, U, L-shaped, etc., including variations on those; and the extensions 82, 84 can be directed at various angles, although for stability during spinning it is preferable that the extensions be arranged in symmetrically opposing directions. These extensions may be fixed or fixable to the conduit 60 or 80 and in fact, the conduit 60 or 80 may in some configurations be an integral part of the receptacle 10 or 40 or the plug 30 or 46.

In yet another example, the chamber 70 may further comprise nodules fixed to the walls of the cavity 76 to position the receptacle therein in a manner to ensure that heat transfer fluid flows uniformly around the outside of the receptacle 10 or 40.

It is thus appreciated that the above descriptions are intended only to serve as examples and many other embodiments are possible within the scope and spirit of the present invention.

The invention claimed is:

1. A receptacle having a proximal end and a distal end, comprising: an outer wall and an inner wall fixed relative to said outer wall, said outer wall and inner wall together defining an annular portion therebetween; and an inner space defined by said inner wall open at each of said proximal end and said distal end, enabling passage of fluid via said inner space whilst holding said fluid within said annular portion, the receptacle further comprising a conduit, adapted for insertion into the inner space so as to allow the fluid to exit therefrom via said conduit, wherein said conduit is configured such that the flowing of a fluid there through imparts rotation to said receptacle.

2. The receptacle according to claim 1, for use in changing the temperature of a biological sample, said sample being characterized by a cross-sectional dimension along which the change of temperature may be performed with a predetermined acceptable resultant quality of the sample, wherein: said annular portion has a distance between said inner wall and said outer wall not exceeding said cross-sectional dimension of the sample.

3. The receptacle according to claim 1, wherein the receptacle has a longitudinal axis, a proximal end and a distal end, and the inner wall defines an inner space extending along said longitudinal axis, and a substantially round cross-section taken perpendicularly to the longitudinal axis, and the inner space is open at both the proximal end and distal end of the receptacle.

4. The receptacle according to claim 1, wherein the inner wall is securely fixed in place within the receptacle and configured sufficient to prevent said inner wall from longitudinal movement with respect to said outer wall.

5. A method of changing the temperature of a liquid sample, comprising:
  a. providing a receptacle having an outer wall and an inner wall fixed relative to said outer wall, said outer wall and inner wall together defining an annular portion therebetween for receiving therein said liquid sample, wherein said receptacle has a longitudinal axis, a proximal end and a distal end, and the inner wall defines an inner space extending along said longitudinal axis, and wherein said annular portion of said receptacle is sealed at the distal end and sealable at the proximal end of the receptacle by a plug having a corresponding annular sealing portion, and further having a bore surrounded by the annular sealing portion, and wherein said bore is adapted to be aligned with the inner space of the receptacle providing a passage thereto:
  b. inserting said liquid sample, at a first temperature, into said annular portion; and
  c. exposing said receptacle to a second temperature different from said first temperature.

6. The method according to claim 5, wherein the liquid is a biological sample comprising sperm.

7. The method according to claim 5, wherein the receptacle has a longitudinal axis and a substantially round cross-section taken perpendicularly to the longitudinal axis.

8. The method according to claim 5, wherein the inner space is open at both the proximal end and distal end of the receptacle.

9. The method according to claim 5, further comprising providing an environment with a temperature gradient in a given direction and wherein step c is performed at least partially by passing the receptacle in said environment along said direction, with the longitudinal axis of the receptacle being parallel to said direction.

10. The method according to claim 5, wherein the plug is made of a resilient material.

11. The method according to claim 5, wherein the method further comprises after step b, sealing the annular portion at the proximal end of the receptacle with the annular sealing portion of the plug.

12. The method according to claim 5, wherein step c comprises providing a heat transfer fluid at the second temperature for flowing around the receptacle and into the inner space via one of the proximal or distal ends and out of the other.

13. The method according to claim 12 further comprising, before step c:
  1. providing a conduit tightly insertable in the inner space of the receptacle at the proximal end thereof, being adapted to direct the heat transfer fluid flowing out of the inner space so as not to enter the annular portion, and
  2. inserting said conduit into the inner space at said proximal end.

14. A method of changing the temperature of a liquid sample, comprising:
  a. providing a receptacle having an outer wall and an inner wall fixed relative to said outer wall, said outer wall and inner wall together defining an annular portion therebetween for receiving therein said liquid sample, wherein said receptacle has a longitudinal axis, a proximal end and a distal end, and the inner wall defines an inner space extending along said longitudinal axis, and wherein said annular portion of said receptacle is sealed at the distal end and sealable at the proximal end of the receptacle by a plug having a corresponding annular sealing portion;
  b. inserting said liquid sample, at a first temperature, into said annular portion; and
  c. exposing said receptacle to a second temperature different from said first temperature;

the method further comprising providing a wand associated with the plug, and wherein the annular portion of the receptacle at the proximal end thereof is sealed by:
   i. inserting the plug into the proximal end of the receptacle so that a portion of said wand enters the annular portion of the receptacle together with said annular sealing portion of the plug, whereby sealing of the annular portion of the receptacle is prevented in the area of contact of the wand with one of the inner or outer walls of the receptacle, and
   ii. removing the wand such that the proximal end of the annular portion of the receptacle becomes fully sealed.

15. A method of changing the temperature of a liquid sample, comprising:
   a. providing a receptacle having an outer wall and an inner wall fixed relative to said outer wall, said outer wall and inner wall together defining an annular portion therebetween for receiving therein said liquid sample;
   b. inserting said liquid sample, at a first temperature, into said annular portion;
   c. providing a conduit tightly insertable in the inner space of the receptacle at the proximal end thereof, being adapted to direct the heat transfer fluid flowing out of the inner space so as not to enter the annular portion, wherein said conduit is configured such that the flowing of the heat transfer fluid therethrough imparts rotation to the receptacle;
   d. inserting said conduit into the inner space at said proximal end; and
   e. exposing said receptacle to a second temperature different from said first temperature and providing a heat transfer fluid at the second temperature for flowing around the receptacle and into the inner space via one of the proximal or distal ends and out of the other.

* * * * *

UNITED STATES PATENT AND TRADEMARK OFFICE
CERTIFICATE OF CORRECTION

PATENT NO. : 7,331,186 B2 Page 1 of 1
APPLICATION NO. : 10/519222
DATED : February 19, 2008
INVENTOR(S) : Amin Arav It is certified that error appears in the above-identified patent and that said Letters Patent is hereby corrected as shown below:

Title Page, Please insert, item:

[60] Provisional application No. 60/391,575, filed on Jun. 27, 2002, and Provisional application No. 60/417,460, filed on Oct. 10, 2002.

Signed and Sealed this

Seventeenth Day of June, 2008

JON W. DUDAS
*Director of the United States Patent and Trademark Office*